United States Patent
Nikam

(10) Patent No.: US 6,191,134 B1
(45) Date of Patent: *Feb. 20, 2001

(54) AMIDE DERIVATIVES OF SUBSTITUTED QUINOXALINE 2, 3-DIONES AS GLUTAMATE RECEPTOR ANTAGONISTS

(75) Inventor: Sham Shridhar Nikam, Ann Arbor, MI (US)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/118,000

(22) PCT Filed: May 20, 1997

(86) PCT No.: PCT/US97/08525

§ 371 Date: Aug. 11, 1998

§ 102(e) Date: Aug. 11, 1998

(87) PCT Pub. No.: WO97/46539

PCT Pub. Date: Dec. 11, 1997

Related U.S. Application Data

(60) Provisional application No. 60/019,377, filed on Jun. 5, 1996.

(51) Int. Cl.[7] .................... A61K 31/498; C07D 241/44

(52) U.S. Cl. .......................................... 514/249; 544/354

(58) Field of Search ............................ 544/354; 514/249

(56) References Cited

U.S. PATENT DOCUMENTS 5,654,303 * 8/1997 Kornberg et al. ............... 514/249
6,080,743 * 6/2000 Acklin et al. ................... 514/249

FOREIGN PATENT DOCUMENTS

9400124 * 1/1994 (WO).
9512417 * 5/1995 (WO).
9609295 * 3/1996 (WO).
9640649 * 12/1996 (WO).
9640650 * 12/1996 (WO).
9640651 * 12/1996 (WO).
9708155 * 3/1997 (WO).
9823599 * 6/1998 (WO).

OTHER PUBLICATIONS

Bigge et al., *Current Opinion Intherapeutic Patents*, pp. 951–989 (1993).*

Klockgether et al, *Annals of Neurology*, vol. 30, pp. 717–723 (1991).*

Klockgether et al., *Annals of Neurology*, vol. 34, pp. 585–593 (1993).*

Frances et al., *Journal of Neurochemistry*, vol. 60, pp. 1589–1604 (1993).*

* cited by examiner

Primary Examiner—Emily Bernhardt
(74) Attorney, Agent, or Firm—Elizabeth M. Anderson

(57) ABSTRACT

A novel series of substituted quinoxaline 2,3-diones useful as neuroprotective agents are taught. Novel intermediates, processes of preparation, and pharmaceutical compositions containing the compounds are also taught. The compounds are glutamate receptor antagonists and are useful in the treatment of stroke, cerebral ischemia, or cerebral infarction resulting from thromboembolic or hemorrhagic stroke, cerebral vasospasms, hypoglycemia, cardiac arrest, status epilepticus, perinatal asphyxia, anoxia, seizure disorders, pain, Alzheimer's, Parkinson's, and Huntington's Diseases.

9 Claims, 3 Drawing Sheets

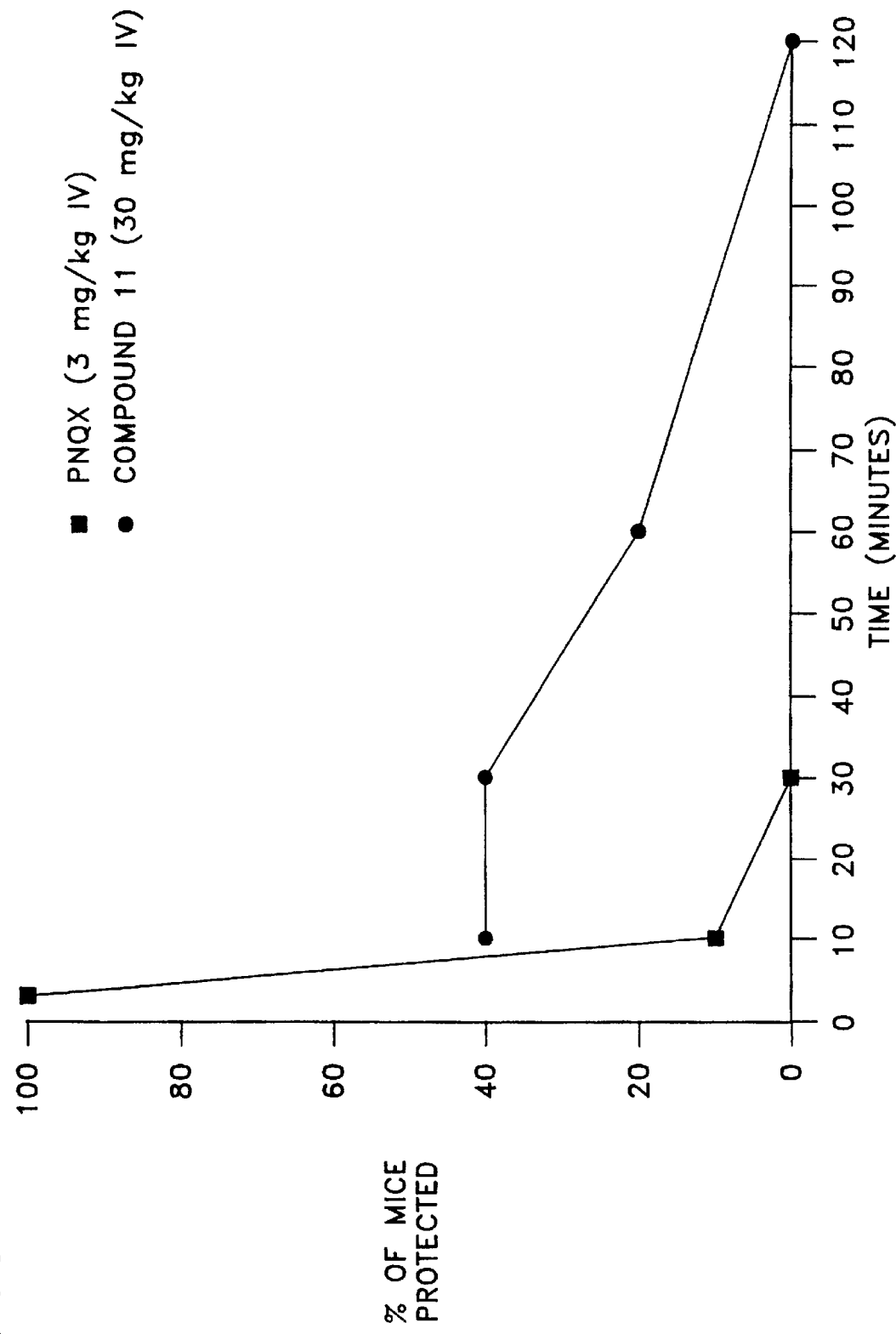

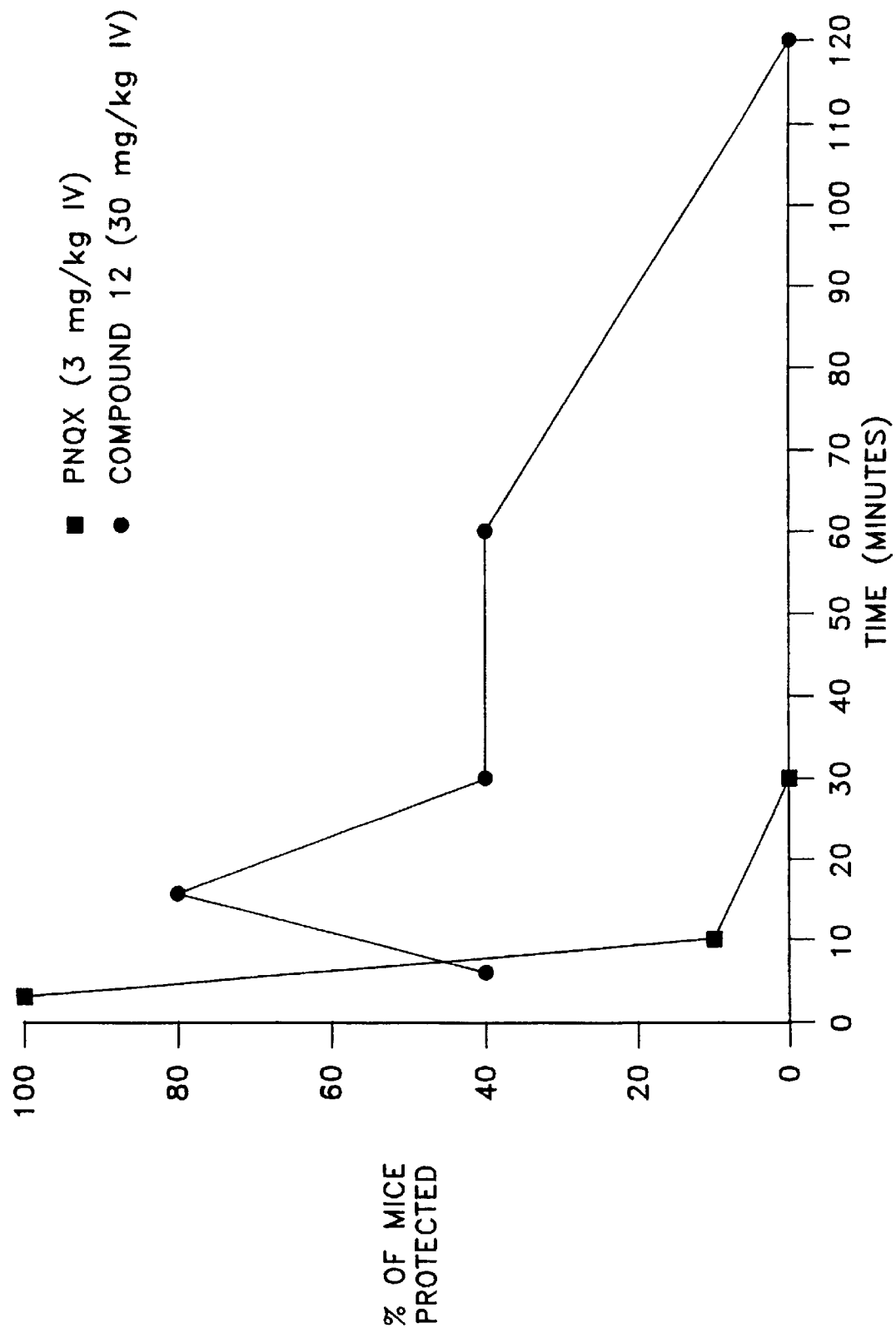

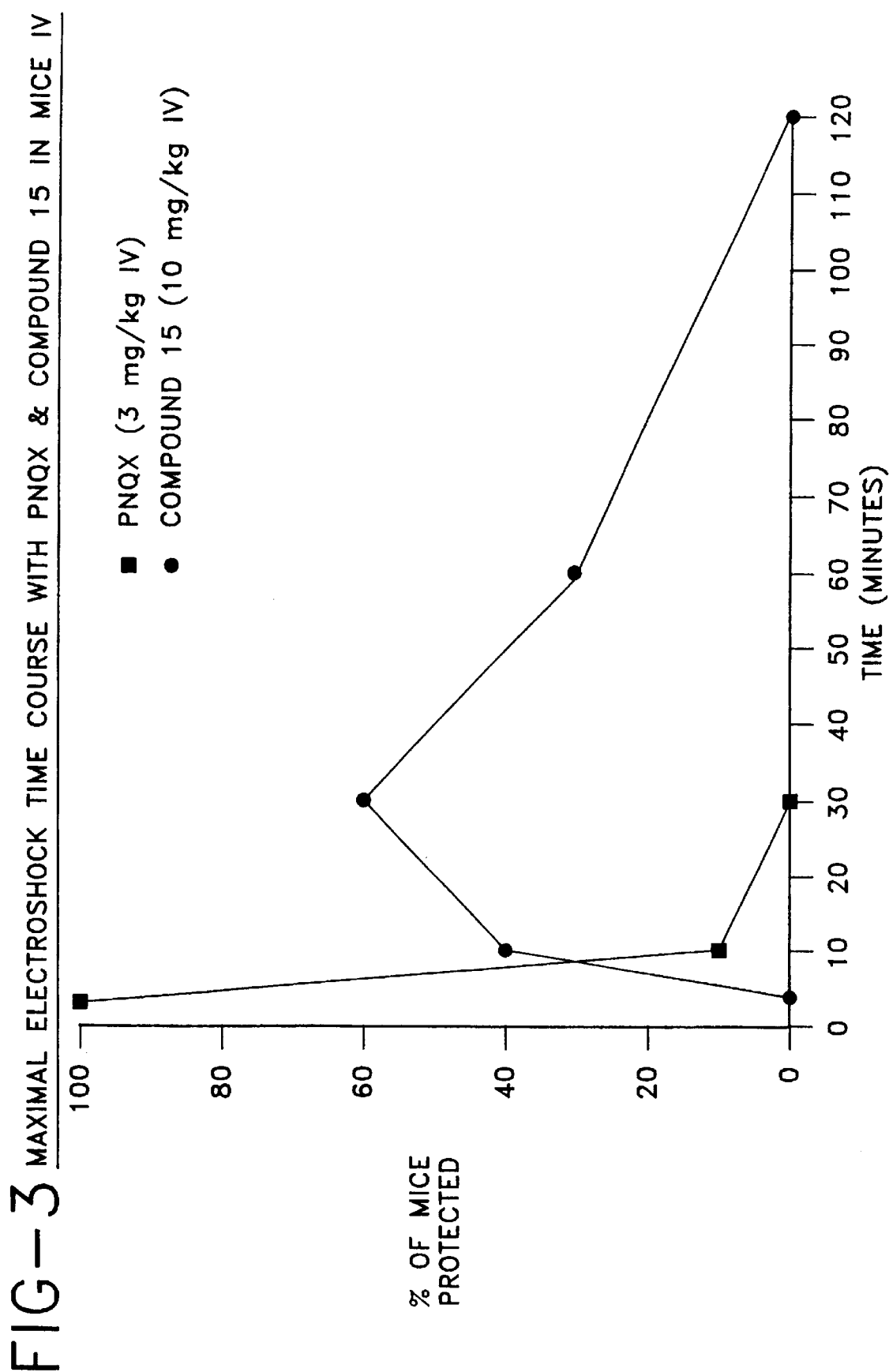

AMIDE DERIVATIVES OF SUBSTITUTED QUINOXALINE 2, 3-DIONES AS GLUTAMATE RECEPTOR ANTAGONISTS

This application is a 371 filing of PCT/US97/08525 filed May 20, 1997, priority based on U.S. Provisional Application No. 60/019,377 filed Jun. 5, 1996.

BACKGROUND OF THE INVENTION

The present invention concerns novel amide derivatives of substituted quinoxaline 2,3-diones having utility as glutamate receptor antagonists. The fused ring quinoxaline 2,3-dione system is substituted at the a- or b-position by amide derivatives. The compounds are active as excitatory amino acid receptor antagonists acting at glutamate receptors, including either or both N-methyl-D-aspartate (NMDA) receptors and non-NMDA receptors such as the α-amino-3-hydroxy-5-methyl-4-isoxazole propionic acid (AMPA) receptor and the kainate receptor. The invention also relates, therefore, to the use of those quinoxaline-2,3-diones as neuroprotective agents for treating conditions such as cerebral ischemia or cerebral infarction resulting from a range of phenomena, such as thromboembolic or hemorrhagic stroke, cerebral vasospasms, hypoglycemia, cardiac arrest, status epilepticus, perinatal asphyxia, anoxia such as from drowning, pulmonary surgery, and cerebral trauma, as well as to treat chronic neurodegenerative disorders such as Alzheimer's Disease, Parkinsonism, and Huntington's Disease, and seizure disorders and pain. The compounds of the present invention may also be useful in the treatment of schizophrenia, epilepsy, anxiety, pain, and drug addiction.

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor, the α-amino-3-hydroxy-5-methyl-4-isoxazole propionic acid (AMPA) receptor, and the kainate receptor. AMPA/kainate receptors may be referred to jointly as non-NMDA receptors. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma, as well as lathyrism, Alzheimer's Disease, Parkinson's Disease, and Huntington's Disease.

Several classes of quinoxalinedione derivatives have been disclosed as glutamate (EAA) receptor antagonists. For example, among excitatory amino acid receptor antagonists recognized for usefulness in the treatment of disorders are those that block AMPA receptors (Bigge C. F. and Malone T. C., *Curr. Opin. Ther. Pat.*, 1993:951; Rogawski M. A., *TiPS*, 1993;14:325). AMPA receptor antagonists have prevented neuronal injury in several models of global cerebral ischemia (Li H. and Buchan A. M., *J. Cerebr. Blood Flow Metab.*, 1993;13:933; Nellgard B. and Wieloch T., *J. Cerebr. Blood Flow Metab.*, 1992;12:2) and focal cerebral ischemia (Bullock R., Graham D. I., Swanson S., and McCulloch J., *J. Cerebr. Blood Flow Metab.*, 1994;14:466; Xue D., Huang Z.-G., Barnes K., Lesiuk H. J., Smith K. E., and Buchan A. M., *J. Cerebr. Blood Flow Metab.*, 1994;14:251). AMPA antagonists have also shown efficacy in models for analgesia (Xu X.-J., Hao J.-X, Seiger A., and Wiesenfeld-Hallin Z., *J. Pharmacol. Exp. Ther.*, 1993;267:140), and epilepsy (Namba T., Morimoto K., Sato K., Yamada N., and Kuroda S., *Brain Res.*, 1994;638:36; Brown S. E. and McCulloch J., *Brain Res.*, 1994;641:10; Yamaguchi S. I., Donevan S. D., and Rogawski M. A., *Epilepsy Res.*, 1993;15:179; Smith S. E., Durmuller N., and Meldrum B. S., *Eur. J. Pharmacol.*, 1991;201:179). AMPA receptor antagonists have also demonstrated promise in chronic neurodegenerative disorders such as Parkinsonism (Klockgether T., Turski L., Honoré T., Zhang Z., Gash D. M., Kurlan R., and Greenamyre J. T., *Ann. Neurol.*, 1993;34(4):585–593).

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain, and anxiety, and may be a significant causal factor in chronic neurodegenerative disorders such as Parkinson's Disease (Klockgether T. and Turski L., *Ann. Neurol.*, 1993;34:585–593), human immunodeficiency virus (HIV) related neuronal injury, amyotrophic lateral sclerosis (ALS), Alzheimer's Disease (Francis P. T., Sims N. R., Procter A. W., and Bowen D. M., *J. Neurochem.*, 1993;60(5):1589–1604), and Huntington's Disease. (See Lipton S., *TINS*, 1993;16(12):527–532; Lipton S. A. and Rosenberg P. A., *New Eng. J. Med.*, 1994;330 (9):613–622; and Bigge C. F., *Biochem. Pharmacol.*, 1993;45:1547–1561 and references cited therein.) NMDA receptor antagonists may also be used to prevent tolerance to opiate analgesia or to help control withdrawal symptoms from addictive drugs (Eur. Pat. Appl. 488,959A).

Copending U.S. Ser. No. 08/124,770 discloses glutamate receptor antagonist quinoxalinedione derivatives represented by the formula:

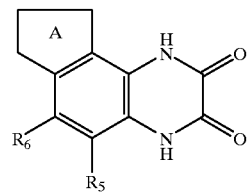

wherein A is a 5 to 7 atom containing ring having a nitrogen which may be substituted by hydrogen, alkyl, or $CH_2CH_2OH$. This application does not disclose or suggest compounds having the instant amides as substituents, or the requisite methodology to prepare the same.

Copending application U.S. Ser. No. 08/404,400 teaches glutamate receptor antagonists which are quinoxalinediones of formula

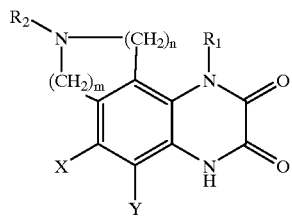

or a pharmaceutically acceptable salt thereof wherein $R_1$ is hydrogen, an alkyl, or an alkylaryl;

X and Y are independently hydrogen, halogen, nitro, cyano, trifluoromethyl, COOH, $CONR_4R_5$ $SO_2CF_3$, $SO_2R_4$, $SONR_4R_5$, alkyl, alkenyl, $(CH_2)_zCONR_4R_5$, $(CH_2)_zCOOR_4$, or $NHCOR_4$, wherein $R_4$ and $R_5$ are independently hydrogen, alkyl having 1 to 6 carbon atoms, cycloalkyl, or alkylaryl, and z is an integer from 0 to 4;

$R_2$ is alkyl$COOR_3$, alkylamine, alkylquanidine, aryl, alkylaryl, COalkyl, COalkylaryl, $CONR_3$alkyl, $CONR_3$aryl, $CONR_3$alkylaryl, $CSNR_3$alkyl, $CSNR_3$alkylaryl or a common amino acid moiety joined by an amide bond, wherein $R_3$ is hydrogen, alkyl, or alkylaryl; and m and n are independently 0, 1, or 2 provided that m+n is >1.

This application does not disclose or suggest the compounds of the instant invention having amides as substituents at the a- or b-positions nor the methodology to prepare them.

JP06228112-A discloses glutamate receptor antagonists which are quinoxaline-2,3(1H,4H)-dione derivatives of formula

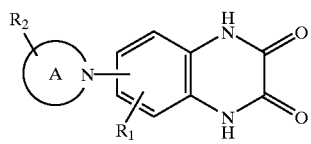

wherein $R_1$ is H, $NO_2$, or $CF_3$;

Ring A is a nitrogen-containing saturated heterocyclic group which may contain sulfur or oxygen;

$R_2$ is H, OH, lower alkoxy, COOH, lower alkoxy carbonyl, $NH_2$, or lower alkoxy carbonyl-amino. This reference does not teach or suggest the instant compounds which must be attached to the quinoxaline dione fused ring system by an alkylene.

WO 93/08188 covers a tricyclic quinoxalinedione of formula

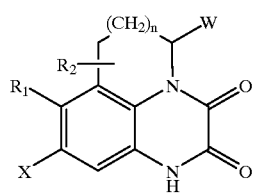

as useful or selective antagonists of glutamate receptors.

European Patent Application 0627434 covers tricyclic quinoxalinedione of Formula I below which are selective antagonists of glycine binding site of the NMDA receptor

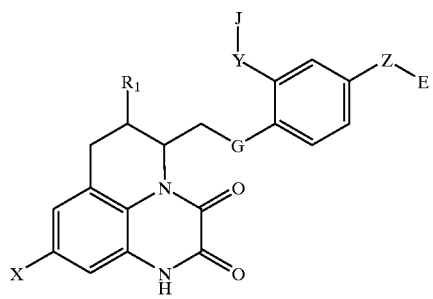

wherein X represents hydrogen, alkyl, halogen, cyano, trifluoromethyl, or nitro;

$R_1$ represents hydrogen, alkyl, cycloalkyl, or cycloalkylalkyl;

G represents —$CONR_2$— or —$NR_2CO$—, wherein $R_2$ represents hydrogen or alkyl;

J represents an acidic group or a group which is convertible thereto in vivo;

E represents a basic group or a group which is convertible thereto in vivo;

Y represents a single bond, alkylene, alkenylene, substituted alkylene, or $Y_1$—Q—$Y_2$, wherein $Y_1$ represents a single bond or alkylene, $Y_2$ represents alkylene, and Q represents a heteroatom selected from oxygen or sulfur; and Z represents alkylene.

WO 94/26747 discloses compounds of Formula I below as useful in the treatment of cerebrovascular disorder

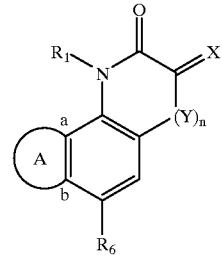

wherein $R_1$ is hydrogen, alkyl or benzyl;

X is O or $NOR_2$, wherein $R_2$ is hydrogen, alkyl, or benzyl;

Y is N—$R_4$, wherein $R_4$ is hydrogen, OH, or alkyl;

n is 0 or 1;

$R_6$ is phenyl, naphthyl, thienyl, pyridyl, all of which may be substituted one or more times with substituents selected from the group consisting of halogen; $CF_3$, $NO_2$, amino, alkyl, alkoxy, and phenyl; and A is a ring of 5 to 7 atoms fused with the benzo ring at the positions marked a and b.

The compounds of the instant invention differ from the art in that they provide noncoplanar compounds with greater aqueous solubility and lipophilicity, therefore, better ability to be formulated as a CNS drug and penetrate the blood-brain barrier. These are important attributes in pharmaceuticals.

An object of this invention is to provide novel quinoxalinediones with amides at the a- or b-positions which function as antagonists.

SUMMARY OF THE INVENTION

The present invention pertains to compounds represented by Formula I:

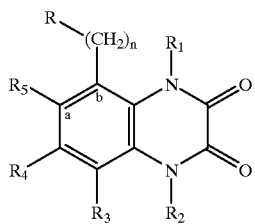

or a pharmaceutically acceptable salt thereof wherein R, $R_1$, $R_2$, $R_3$, $R_4$, $R_5$, and n are as described below.

The present invention also pertains to a pharmaceutical composition containing the compound defined by Formula I in an amount effective to treat cerebrovascular disorders responsive to the blockade of glutamate receptors (such as the α-amino-3-hydroxy-5-methyl-4-isoxazole propionic acid (AMPA) receptor and the kainate receptor), and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's Disease, Amyotrophic Lateral Sclerosis (ALS), Parkinsonism, and Alzheimer's Disease. The pharmaceutical composition of this invention may also be employed as an analgesic or the treatment of epilepsy.

The invention further relates to a method of treating cerebrovascular disorders responsive to the antagonism of glutamate or aspartate receptors in a human by administering a therapeutically effective amount of the 2,3-quinoxalinediones of this invention and further to administering said compound in a unit dosage form.

The invention further relates to novel methods of preparing the 2,3-quinoxalinediones and to novel intermediates useful in their preparation.

BRIEF DESCRIPTION OF THE DRAWINGS

FIG. 1. Maximal Electroshock Time Course With Compound 11 in Mice IV.

FIG. 2. Maximal Electroshock Time With Compound 12 in Mice IV.

FIG. 3. Maximal Electroshock Time Course With PNQX, and Compound 15 in Mice IV.

DETAILED DESCRIPTION OF THE INVENTION

The substituted quinoxaline-2,3-diones of the instant invention are those of Formula I

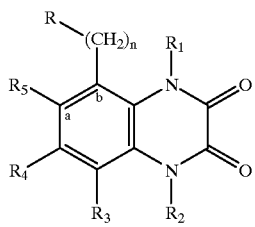

or a pharmaceutically acceptable salt thereof wherein
R is an amide;
n is an integer of from 1 to 4;

$R_1$ is hydrogen, alkyl, aralkyl, carboxyalkyl, phosphoroalkyl, or phosphonoalkyl;

$R_2$ is hydrogen, hydroxy, or amino;

$R_3$ and $R_4$ are each independently hydrogen, alkyl, cycloalkyl, alkenyl, aryl, heteroaryl, halogen, haloalkyl, nitro, cyano, $SO_2CF_3$, $CH_2SO_2R_6$, $(CH_2)_mCO_2R_6$, $(CH_2)_mCONR_7R_8$, $(CH_2)_mSO_2NR_7R_8$, or $NHCOR_6$ wherein m is an integer of from 0 to 4, and $R_6$, $R_7$, and $R_8$ are each independently selected from hydrogen, alkyl, cycloalkyl, haloalkyl, or aralkyl;

$R_5$ is hydrogen, alkyl, alkenyl, cycloalkyl, halogen, haloalkyl, aryl, aralkyl, heteroaryl, heteroaralkyl, nitro, cyano, $SO_2CF_3$, $(CH_2)_mCO_2R_9$, $(CH_2)_mCONR_9R_{10}$, $SONR_9R_{10}$, or $NHCOR_9$;

m is an integer of from 0 to 4;

$R_9$ and $R_{10}$ are each independently hydrogen, alkyl, cycloalkyl, haloalkyl, or aralkyl; and $R_5$ may be at the a-position and R—$(CH_2)_n$— at the b-position on the ring.

Preferred compounds are those of Formula I wherein R is a straight chain amide

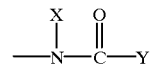

or an amide in a mono- or bi-cyclic ring, unsubstituted or substituted by from 1 to 4 substituents, and is

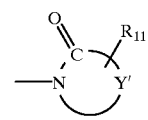

of from 4 to 7 atoms or

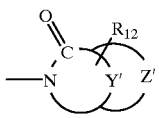

of from 8 to 12 atoms
attached at N to the quinoxaline ring through —$(CH_2)_n$— at the a- or b-position, wherein $R_{11}$ and $R_{12}$ are each independently 1 to 4 substituents independently selected from hydrogen, hydroxy, hydroxyalkyl, alkyl, alkoxy, alkoxyalkyl, —$NR_{13}R_{14}$, aminoalkyl, alkenyl, alkynyl, thiol, thioalkyl, alkylthioalkyl, aryl, aralkyl, heteroaryl, heteroaralkyl, heterocycloalkyl, cycloalkyl, $C(O)R_{15}$, —$SO_2R_{15}$, —$SO_2NR_{13}R_{14}$, —$(CH_2)_nSO_2NR_{13}R_{14}$, and —$(CH_2)_nSO_2R_{15}$; wherein $R_{13}$ and $R_{14}$ are independently selected from hydrogen, alkyl, cycloalkyl, heterocycloalkyl, aralkyl, and aryl; $R_{15}$ is hydroxy, alkoxy, —$NR_{13}R_{14}$, or haloalkyl; or $R_{11}$ may be 2 substituents attached at the same carbon;

X is hydrogen, alkyl, aralkyl, aryl, heteroaryl, cycloalkyl, heterocycloalkyl, alkenylalkyl, alkylalkenylalkyl, alkynylalkyl, alkylhydroxyalkyl, alkylaminoalkyl;

Y is alkyl, haloalkyl, alkenylalkyl, alkylalkenylalkyl, alkynylalkyl, alkylalkynylalkyl, cycloalkyl, heterocycloalkyl, alkoxy, alkoxyalkyl, thioalkyl, alkylthioalkyl;

or is alkylaminoalkyl or arylaminoalkyl such as —(CH)$_p$(R$_{16}$)NR$_{17}$R$_{18}$, wherein p is an integer of from 1 to 6, R$_{16}$ is hydrogen, alkyl, aryl, aralkyl, and R$_{17}$ and R$_{18}$ are each independently hydrogen, alkyl, aralkyl, aryl, heteroaryl or joined together to form a saturated ring of from 4 to 7 members;

or is a natural or unnatural amino acid ((α-, β-, or γ-) backbone such as —(C*H)$_q$(R$_{19}$)NR$_{20}$R$_{21}$ wherein the C* stereochemistry is R or S or RS. q is an integer of from 1 to 3, R$_{19}$ is hydrogen or a side chain of a natural or unnatural amino acid, R$_{20}$ and R$_{21}$ are independently hydrogen, alkyl, aralkyl, alkoxycarbonyl, and aralkoxycarbonyl;

or is carboxyalkyl or alkylcarboxyalkyl such as —(CH)$_p$(R$_{22}$)CO$_2$R$_{23}$ wherein p is an integer of from 1 to 6, R$_{22}$ is hydrogen, alkyl, aryl, aralkyl, R$_{23}$ is hydrogen, alkyl, aralkyl, aryl, heteroaryl;

or is a side-chain amide such as —(CH)$_p$(R$_{24}$)C(O)NR$_{25}$R$_{26}$ wherein p is an integer of from 1 to 6, R$_{24}$ is hydrogen, alkyl, aralkyl, aryl, and R$_{25}$ and R$_{26}$ are each independently hydrogen, alkyl, aralkyl, aryl, heteroaryl or joined together to form a saturated ring of from 5 to 7 members;

or is alkylheterocycloalkyl or alkylheteroaralkyl such as —(CH$_2$)$_q$—R$_{27}$ wherein q is an integer from 1 to 3 and R$_{27}$ is a 4- to 7-membered O, N, or S heterocycle such as oxazolyl, oxadiazolyl, thiazolyl, 1,3,4-oxadiazolyl, 1,2,4-triazolyl, 1,3,4-thiadiazolyl, pyrrazolyl, imidazolyl, tetrazolyl, 1,3-oxazolyl, isooxazolyl, 1,2,3-triazolyl, 1,3,4-thiazolyl, or is amino heterocycle —NR$_{27a}$—R$_{27b}$ wherein 27a is hydrogen or alkyl, and 27b is as described in R$_{27}$;

Y' and Z' are each independently carbon which is substituted by hydrogen, halogen, haloalkyl, alkyl, alkoxy, alkoxyalkyl, NR$_{13}$R$_{14}$, aminoalkyl, aralkyl, aryl, heteroaryl, heteroaralkyl, cycloalkyl, heterocycloalkyl, hydroxy, and hydroxyalkyl, —O—, —S—, —SO—, —SO$_2$—, —NR$_{28}$—, wherein R$_{28}$ is alkyl, hydrogen, aralkyl, heteroaralkyl, aryl, heteroaryl, cycloalkyl, heterocycloalkyl, —C(O)OR$_{29}$, —C(O)R$_{29}$, —SO$_2$R$_{30}$, —SO$_2$NR$_{31}$R$_{32}$, —CH$_2$SO$_2$R$_{30}$, —CH$_2$SO$_2$NR$_{31}$R$_{32}$, wherein R$_{29}$ is alkyl, aralkyl, cycloalkyl, heterocycloalkyl, aryl, or heteroaryl; R$_{30}$ is alkyl, aralkyl, hydroxyl, or alkoxy; and R$_{31}$ and R$_{32}$ are each independently hydrogen and alkyl.

Bicyclic structures encompassed in this invention include spiro ring structures, wherein both ends of a second ring are attached to the same carbon unit on the parent ring.

For monocyclic and bicyclic structures wherein X or Y represent a carbon atom, the structure may also include an integral double bond.

More preferred compounds of Formula I wherein R is an amide

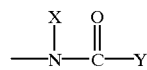

are those wherein
X is selected from hydrogen, alkyl, aralkyl, aryl, heteroaryl, cycloalkyl, heterocycloalkyl, and
Y is selected from alkyl, haloalkyl, cycloalkyl, heterocycloalkyl, alkynyl, alkenyl, aryl, heteroaryl, alkoxy, alkoxyalkyl, alkylaminoalkyl, carboxyalkyl;
or is a side-chain amide such as —(CH)$_p$(R$_{24}$)C(O)NR$_{25}$R$_{26}$ wherein p is an integer of from 1 to 6, R$_{24}$ is hydrogen, alkyl, aralkyl, aryl, and R$_{25}$ and R$_{26}$ are each independently hydrogen, alkyl, aralkyl, aryl, heteroaryl, alkoxycarbonyl, aralkoxycarbonyl or joined together to form a saturated ring of from 5 to 7 members;

or is a heteroalkyl such as —(CH$_2$)$_q$—R$_{27}$ wherein q is an integer from 1 to 3 and R$_{27b}$ is a 4- to 7-membered oxygen, nitrogen, sulfur heterocycle with 1- to 4 heteroatoms such as oxadiazolyl, thiazolyl, oxazolyl, and tetrazolyl.

Still more preferred are those of Formula I wherein R is an amide

wherein
X is selected from hydrogen, methyl, ethyl, isopropyl, and butyl and
Y is selected from methyl, ethyl, isopropyl, propyl, butyl, benzyl, allyl, propargyl, cyclopentyl, cyclohexyl, 2- or 3-pyrrolidinyl, 2- or 3-tetrahydrofuranyl, 2-, 3-, or 4-piperidinyl, substituted phenyl, 2- or 3-furanyl, 2- or 3-thienyl, 2- or 3-benzofuranyl, 2- or 3-benzthienyl, 2- or 3-indolyl, 2-benzimidazolyl, imidazolyl, 3- or 4-piperidinyl, phenyl, 2- or 3-indolyl, tetrazolyl, imidazolyl, pyrrazolyl, naphthyl, oxadiazolyl, and 2-benzimidazolyl.

More preferred compounds of Formula I wherein R is an amide in a mono- or bi-cyclic ring, unsubstituted or substituted by from 1 to 4 substituents, and is

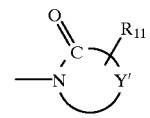

of from 4 to 7 atoms

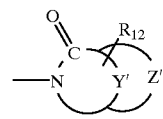

of from 8 to 12 atoms
are those wherein R is a mono-cyclic ring of from 4 to 7 atoms and Y' is methylene, O, S, or N—R$_{28}$ wherein R$_{28}$ is H, alkyl, aryl.

The open chain amides are preferred over the mono- and bicyclic amides.

Most preferred compounds of Formula I are selected from
N-Methyl-N-(6-methyl-7-nitro-2,3-dioxo-1,2,3,4-tetrahydro-quinoxalin-5-ylmethyl)-acetamide,
5-(Isopropyl-methyl-amino)-methyl-6-methyl-7-nitro-1,4-dihydro-quinoxaline-2,3-dione,
Cyclohexanecarboxylic acid-methyl- (6-methyl-7-nitro-2,3-dioxo-1,2,3,4-tetrahydro-quinoxalin-5-ylmethyl) amide,
5-(Cyclohexylmethyl-methyl-amino)-6-methyl-7-nitro-1,4-dihydro-quinoxaline-2,3-dione,
N-methyl-N-(6-methyl-7-nitro-2,3-dioxo-1,2,3,4-tetrahydro-quinoxalin-5-ylmethyl)-2-phenyl-acetamide, N-methyl-N-(6-methyl-7-nitro-2,3-dioxo-1,2,3,4-tetrahydro-quinoxalin-5-ylmethyl)-benzamide, 4-Chloro-N-methyl-N-(6-Methyl-7-nitro-2,3-dioxo-1,2,3,4-tetrahydro-quinoxalin-5-ylmethyl)-benzamide, N-Methyl-N-(6-Methyl-7-nitro-2,3-dioxo-1,2,3,4-tetrahydro-quinoxalin-5-ylmethyl)-4-trifluoromethyl-benzamide, 3,4-Dichloro-N-methyl-N-(6-methyl-7-nitro-2,3-dioxo-1,2,3,4-tetrahydro-quinoxalin-5-ylmethyl)-benzamide, N-Methyl-N-(6-Methyl-7-nitro-2,3-dioxo-1,2,3,4-tetrahydro-quinoxalin-5-ylmethyl)-4-nitro-benzamide, Thiophene-2-carboxylic acid-methyl- (6-methyl-7-nitro-2,3-dioxo-1,2,3,4-tetrahydro-quinoxalin-5-ylmethyl)-amide, Furan-2-carboxylic acid methyl-(6-methyl-7-nitro-2,3-dioxo-1,2,3,4-tetrahydro-quinoxalin-5-ylmethyl)-amide, Benzo[b]thiophene-2-carboxylic acid methyl-(6-methyl-7-nitro-2,3-dioxo-1,2,3,4-tetrahydro-quinoxalin-5-ylmethyl)-amide, 4-Methoxy-N-methyl-N-(6-methyl-7-nitro-2,3-dioxo-1,2,3,4-tetrahydro-quinoxalin-5-ylmethyl)-benzamide, and N,N,N'-Trimethyl-N'-(6-Methyl-7-nitro-2,3-dioxo-1,2,3,4-tetrahydro-quinoxalin-5-ylmethyl)-succinamide.

The compounds of Formula I are capable of further forming pharmaceutically acceptable acid addition salts. These forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, isethionate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediaunine, chloroprocaine, choline, diethanolamine, ethylenediamine, N-methylglucamine, and procaine (see, for example, Berge S. M., et al., "Pharmaceutical Salts," Ibid.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as a mixture of cis and trans isomers or as the individual cis and trans isomers or R and S stereoisomers. The mixture of isomers as well as the individual isomers are intended to be encompassed within the scope of the present invention.

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyl" means a saturated carbocycle of from about 5 to about 7 carbons.

The term "carboxyalkyl" means alkyl as above and attached to a carboxy group.

The term "phosphoroalkyl" means alkyl as above and attached to a phosphoro group.

The term "phosphonoalkyl" means alkyl as above and attached to a phosphono group.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

Alkynyl means a straight or branched unsaturated hydrocarbon radical of from 2 to 6 carbon atoms and includes but is not limited to ethynyl, 2,3-propynyl, 1,2-propynyl, and 3,4-butynyl.

"Alkoxy" is O-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "aralkyl" means aryl and alkyl as defined above and includes but is not limited to benzyl, 2-phenylethyl, and 3-phenylpropyl; a preferred group is phenyl.

The term "heteroaryl" means a heteroaromatic radical which is 2-, 3-, or 4-pyridinyl, 2-, 4-, or 5-pyrimidinyl, 2- or 3-thienyl, isoquinolines, quinolines, imidazolines, pyrroles, indoles, and thiazoles.

"Halogen" is fluorine, chlorine, bromine, or iodine.

The term "haloalkyl" means halogen and alkyl as defined above, for example, but not limited to, trifluoromethyl and trichloromethyl.

"Alkylaryl" means aryl as defined above and alkyl as defined above, for example, but not limited to benzyl, 2-phenylethyl, 3-phenylpropyl; a preferred group is benzyl.

The term "heterocycloalkyl" means a nonaromatic ring with from 4 to 7 members, with up to 4 heteroatoms for example, N, O, and S.

The term "amino" means a primary or secondary amino group.

The term "thioalkyl" means a S-alkyl of from 1 to 6 carbon atoms as defined above for "alkyl".

The term "heteroaralkyl" means alkyl as above attached to a nitrogen, oxygen, or sulfur heteroaromatic radical such as 2-, 3-, or 4-pyridinyl, 2-, 4-, or 5-pyrimidinyl, 2-, 3-thienyl, isoquinolinyl, quinolinyl, indolyl, imidazolyl, pyrrolyl, and thiazolyl

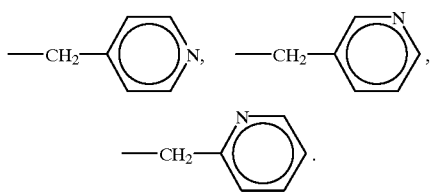

The term "alkoxyalkyl" means alkyl as above and attached to an alkoxy group of up to 6 carbons.

The term "aminoalkyl" means alkyl as above and attached to an amino group as described above.

The term "alkenylalkyl" means alkyl group as above and attached to an alkenyl group as above.

The term "alkylalkenylalkyl" means alkyl group as above attached to a non-terminal alkenyl group as described above. The alkylalkenyl group alkyl group of up to 8 carbon atoms.

The term "alkynylalkyl" means alkyl group as above attached to an alkynyl group as above.

The term "alkylhydroxyalkyl" means alkyl group as above attached to a secondary or tertiary alcohol moiety bearing up to 8 carbon atoms.

The term "alkylaminoalkyl" means alkyl group as above attached to a secondary or tertiary amino group.

The term "thioalkyl" means alkyl group as above attached to a thiol group.

The term "alkylthioalkyl" means alkyl group as above attached to a thioalkyl group.

Common amino acid moiety means the naturally occurring α-amino acids, unnatural amino acids, substituted β, γ, δ amino acids and their enantiomers.

Common amino acids are: Alanine, β-alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Modified and unusual amino acids are as would occur to a skilled chemist and are, for example, but not limited to:

10,11-Dihydro-5H-dibenzo[a,d]cyclohepten-5-yl)glycine or a-Amino-10,11-dihydro-5H-dibenzo[a,d] cycloheptene-5-acetic acid (Paraphenyl)phenylalanine, 3,3-Diphenylalanine, 3-Hydroxyproline, 4-Hydroxyproline, N-Methylphenylalanine, N-Methylaspartic acid, N-Methylisoleucine, N-Methylvaline, Norvaline, Norleucine, Ornithine, 2-Aminobutyric acid, 2-Amino-4-pentanoic acid (Allylglycine), $N^G$-nitroarginine, 2-Amino-3-(2-amino-5-thiazole)propanoic acid, 2-Amino-3-cyclopropanepropanoic acid Cyclopropylalanine), Cyclohexylalanine (Hexahydrophenylalanine), N-Methylcyclohexylalanine (N-Methylhexahydrophenylalanine), 2-Amino-4,4(RS)-epoxy-4-pentanoic acid, $N^{im}$-2,4-Dinitrophenylhistidine, 2-Aminoadipic acid, 2-Amino-5-phenylpentanoic acid (Homophenylalanine), Methionine sulfoxide, Methionine sulfone, 3-(1'-Naphthyl)alanine, 3-(2'-Naphthyl)alanine, 2-Amino-3-cyanopropanoic acid (Cyanoalanine), Phenylglycine, 2-Aminopentanoic acid (Propylglycine), 2-Amino-6-(1-pyrrollo)-hexanoic acid, 2-Amino-3-(3-pyridyl)-propanoic acid (3-Pyridylalanine), 1,2,3,4-Tetrahydro-3-isoquinolinecarboxylic acid, 2-Amino-3-(4-thiazolyl)-propanoic acid, O-Tertiary butyl-tyrosine, O-Methyl-tyrosine, O-Ethyl-tyrosine, $N^{in}$-Formyl-tryptophan, 5H-Dibenzo[a,d]cycloheptene glycine, 9H-Thioxanthene glycine, and 9H-Xanthene glycine.

Spiro rings include but are not limited to 5- to 7-membered carbocyclic or heterocyclic ring with up to 4 heteroatoms.

The compounds of the invention exhibit valuable biological properties because of their strong excitatory amino acid (EAA) antagonizing properties at one of several binding sites on glutamate receptors: the AMPA ((RS)-amino-3-hydroxy-5-methyl-4-isoxazole propionic acid (or kainic acid) binding site on AMPA (non-NMDA) receptors or the glycine site of NMDA receptors.

The compounds of the present invention exhibit binding affinity for the AMPA receptors measured as described in Honoré T., et al., *Neuroscience Letters*, 1985;54:27–32. Preferred compounds demonstrate $IC_{50}$ values <100 μM in this assay. The compounds of the present invention exhibit binding affinity for the kainate site (non-NMDA receptor) measured as described in London E. D. and Coyle J., *Mol. Pharmacol.*, 1979;15:492. The compounds of the present invention exhibit binding affinity for the glycine (GLY) site of the NMDA receptor measured as described in Jones S. M., et al., *Pharmacol. Methods*, 1989;21:161. To measure functional AMPA antagonist activity, the effects of the agent on AMPA-induced neuronal damage in primary cortical neuronal cultures was examined using techniques similar to those outlined by Koh J.-Y., et al.,*J. Neurosci.*, 1990;10:693. In addition, the neuronal damage produced by long-term exposure to 100 μM AMPA may be measured by the release of the cytosolic enzyme lactate dehydrogenase (LDH).

Selected compounds of the present invention were tested by one or more of the above-described assays. The data obtained in the assays is set forth in Table 1 below. The $IC_{50}$ values are a measure of the concentration (μM) of the test substance which inhibits 50% of an induced release from the tested receptors.

TABLE 1

| | Quinoxaline 2,3-diones | | |
| --- | --- | --- | --- |
| | | $IC_{50}$ (μM) | |
| Compound | AMPA | KA | GLY |
| 1. N-Methyl-N-(6-methyl-7-nitro-2,3-dioxo-1,2,3,4-tetrahydro-quinoxalin-5-ylmethyl)-acetamide | 0.35 | 1.66 | 0.03 |

TABLE 1-continued

Quinoxaline 2,3-diones

| | | IC$_{50}$ ($\mu$M) | | |
|---|---|---|---|---|
| | Compound | AMPA | KA | GLY |
| 2. | 5-(Isopropyl-methyl-amino)-methyl-6-methyl-7-nitro-1,4-dihydro-quinoxaline-2,3-dione | 1.26 | 11.97 | — |
| 3. | Cyclohexanecarboxylic acid-methyl-(6-methyl-7-nitro-2,3-dioxo-1,2,3,4-tetrahydro-quinoxalin-5-ylmethyl)amide | 0.91 | 3.21 | 0.3 |
| 4. | 2-Cyclohexyl-N-methyl-N-(6-methyl-7-nitro-2,3-dioxo-1,2,3,4 tetrahydro-quinoxalin-5-ylmethyl)-acetamide | 2.05 | 2.97 | 0.2 |
| 5. | N-methyl-N-(6-methyl-7-nitro-2,3-dioxo-1,2,3,4-tetrahydro-quinoxalin-5-ylmethyl)-2-phenyl-acetamide | 0.35 | 0.59 | 0.02 |
| 6. | N-methyl-N-(6-methyl-7-nitro-2,3-dioxo-1,2,3,4-tetrahydro-quinoxalin-5-ylmethyl)-benzamide | 1.22 | 2.77 | 0.03 |
| 7. | 4-Chloro-N-methyl-N-(6-Methyl-7-nitro-2,3-dioxo-1,2,3,4-tetrahydro-quinoxalin-5-ylmethyl)-benzamide | 0.98 | 1.98 | 0.04 |
| 8. | N-Methyl-N-(6-Methyl-7-nitro-2,3-dioxo-1,2,3,4-tetrahydro-quinoxalin-5-ylmethyl)-4-trifluoromethyl-benzamide | 1.92 | 3.70 | — |
| 9. | 3,4-Dichloro-N-methyl-N-(6-methyl-7-nitro-2,3-dioxo-1,2,3,4-tetrahydro-quinoxalin-5-ylmethyl)-benzamide | 1.69 | 3.45 | — |
| 10. | N-Methyl-N-(6-Methyl-7-nitro-2,3-dioxo-1,2,3,4-tetrahydro-quinoxalin-5-ylmethyl)-4-nitro-benzamide | 1.12 | 0.95 | — |
| 11. | Thiophene-2-carboxylic acid-methyl-(6-methyl-7-nitro-2,3-dioxo-1,2,3,4-tetrahydro-quinoxalin-5-ylmethyl)-amide | 0.46 | 1.23 | 0.008 |
| 12. | Furan-2-carboxylic acid methyl-(6-methyl-7-nitro-2,3-dioxo-1,2,3,4-tetrahydro-quinoxalin-5-ylmethyl)-amide | 0.38 | 1.21 | 0.006 |
| 13. | Benzo[b]thiophene-2-carboxylic acid methyl-(6-methyl-7-nitro-2,3-dioxo-1,2,3,4-tetrahydro-quinoxalin-5-ylmethyl)-amide | 0.62 | 5.98 | 0.04 |
| 14. | 4-Methoxy-N-methyl-N-(6-methyl-7-nitro-2,3-dioxo-1,2,3,4-tetrahydro-quinoxalin-5-ylmethyl)-benzamide | 0.52 | 0.85 | 0.005 |
| 15. | Methyl-(6-methyl-7-nitro-2,3-dioxo-1,2,3,4-tetrahydro-quinoxalin-5-ylmethyl)-carbamic acid ethyl ester | 0.21 | 0.29 | 0.10 |

Additionally, as a preliminary indicator of in vivo CNS activity related to anticonvulsant activity and potential neuroprotection, a maximal electroshock assay in CF-1 strain mice (20–25 g) was performed with corneal electrodes by conventional methods as described previously (Krall, et al., *Epileisia*, 1988;19:409–428). The compounds of this invention generally demonstrated ED$_{50}$ values of <50 mg/kg.

MES (IV) Data for Compound 11 from Table 1

TABLE 2

Compound 11; MES Data

| Time (min) | Dose (mg/kg) | Protected (%) | Ataxic (%) |
|---|---|---|---|
| 5 | 10 | 0 | 0 |
| | 30 | 40 | 40 |
| 15 | 10 | 40 | 0 |
| | 30 | 80 | 60 |
| 30 | 10 | 40 | 0 |
| | 30 | 40 | 20 |
| 60 | 10 | 0 | 0 |
| | 30 | 40 | 20 |

MES (IV) Data for Compound 12 from Table 1

TABLE 3

Compound 12; MES Data

| Time (min) | Dose (mg/kg) | Protected (%) | Ataxic (%) |
|---|---|---|---|
| 3 | 30 | 40 | 40 |
| 15 | 10 | 40 | 0 |
| | 30 | 80 | 60 |
| 30 | 10 | 40 | |
| | 30 | 40 | 20 |
| 60 | 30 | 40 | 20 |

MES (IV) Data for Compound 15 from Table 1

TABLE 4

Compound 15; MES Data

| Time (min) | Dose (mg/kg) | Protected (%) | Ataxic (%) |
|---|---|---|---|
| 10 | 3 | 0 | 0 |
|  | 10 | 40 | 0 |
| 30 | 3 | 0 | 0 |
|  | 10 | 60 | 0 |

FIGS. 1, 2, and 3 show the maximal electroshock time course with Compounds 11, 12, and 15, respectively, of the instant invention and the standard PNQX in ten mice given in a dose of 30 mg/kg IV. The graph is the percent of mice protected versus the time in minutes.

In particular see FIGS. 1 and 2 wherein, when compared with the standard, a tricyclic quinoxalinedione AMPA antagonist 1,4,7,8,9,10-hexahydro-9-methyl-6-nitropyrido[3,4-f]quinoxaline-2,3-dione methane sulfonate (PNQX), Compounds 11 and 12 of the instant invention show extended duration of action.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprises conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, and accordingly suitable representative unit dosage forms.

Solid forms of pharmaceutical compositions for PO administration and injectable solutions are preferred.

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid-dependent anoxia, excitatory amino-acid-dependent ischemia, excitatory amino-acid-dependent Parkinsonism, excitatory amino-acid-dependent convulsions, and excitatory amino-acid-dependent migraine. Suitable dosage ranges are 0.1 to 1000 mg daily, 10 to 50 mg daily, and especially 30 to 100 mg daily, dependent as usual upon the exact mode of administration, form in which administered, the indication toward which the administration is directed, the subject involved, and the body weight of the subject involved, and further, the preference and experience of the physician or veterinarian in charge.

The schemes and examples which follow are intended as an illustration of certain preferred embodiments of the invention, and no limitation of the invention is implied.

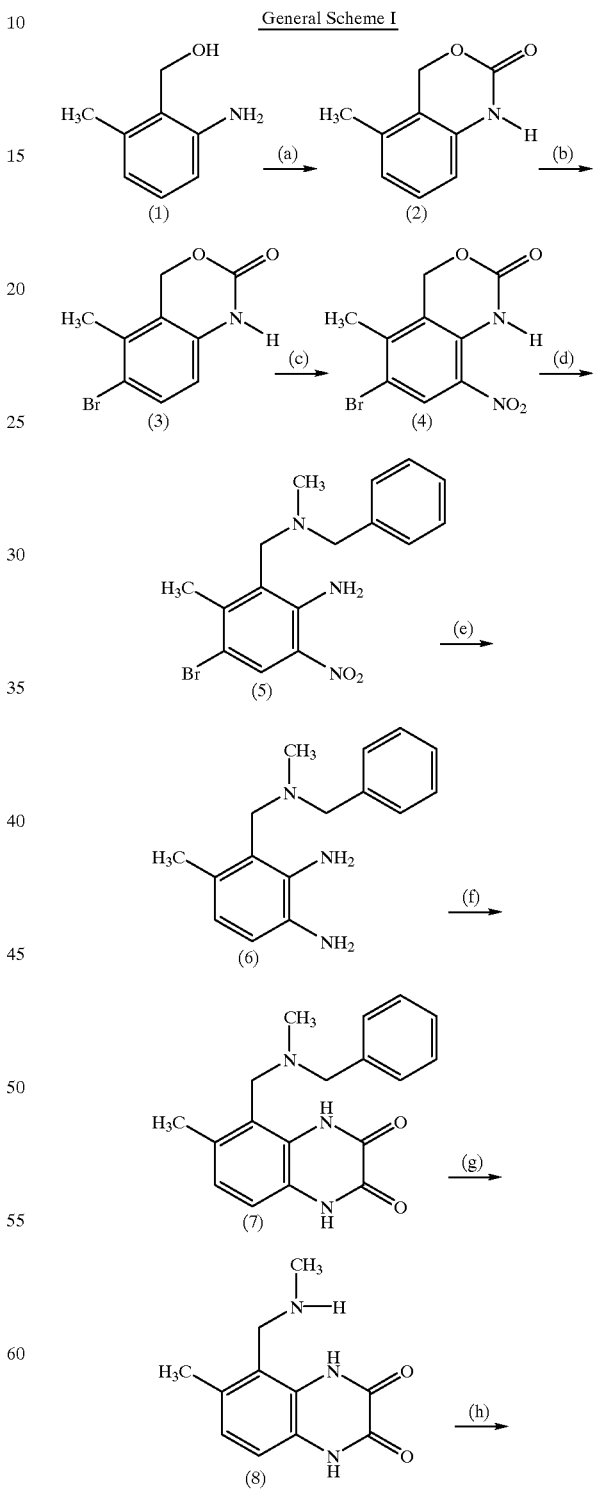

General Scheme I

-continued

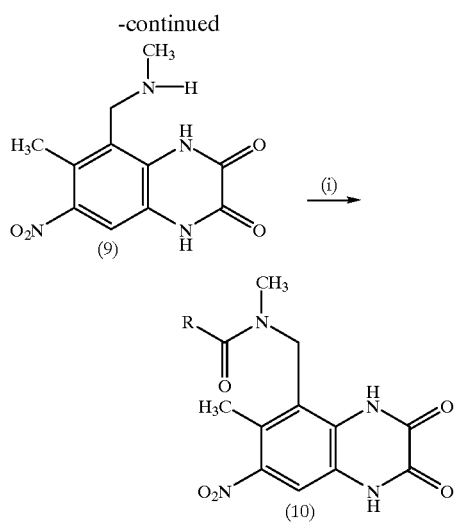

Step (a) of Scheme I above involves reacting aminobenzyl alcohol derivative of Formula (1) with a reactive acylating agent, preferably phosgene in the presence of a tertiary base like triethylamine in a ethereal solvent, preferably THF at temperatures ranging from −10° C. to room temperature. The reaction mixture is stirred for 2 to 16 hours and diluted with water. Product is extracted with water insoluble solvent like ethyl acetate. The extracts washed with water and brine and dried over $MgSO_4$. The product was crystallized from solvent mixture, preferably EtOAc and pet. ether.

Step (b) involves bromination of the cyclic carbamate derivative of Formula (2) with a brominating agent like bromine in an acidic solvent mixture like AcOH and TFA. The reaction is done at temperatures between 10° C. to room temperatures. Reaction mixture is stirred for around 2 hours and poured over ice water. The precipitate is filtered and dried at elevated temperatures, preferably at 120° C.

Step (c) involves the nitration of the bromo cyclic carbamate derivative as shown in Formula (3) with a nitrating agent like nitric acid or potassium nitrate, preferably potassium nitrate in an acidic solvent like sulfuric acid at temperatures between 0° C. to room temperature. Reaction carried out for 4 to 16 hours, preferably around 14 hours and poured over ice. The precipitate was filtered and air dried to give the desired product.

Step (d) involves the reaction of the nitro cyclic carbamate derivative as shown in Formula (4) with a secondary amine, preferably N-methyl-benzylamine. Reaction is carried out at elevated temperatures between 100° C. to 180° C. with or with a solvent like N-methyl-formamide, preferably without a solvent for about 18 hours. Volatile materials were evaporated under reduced pressure and the product isolated from the crude via column chromatography using pet. ether:EtOAc as the solvent mixture to give the desired benzylamine derivative, or via crystallization.

Step (e) involves the hydrogenation ($H_2$, around 50 psi) of the benzylamine derivative as shown in Formula (5) in the presence of a catalyst like Ra Ni and a base, preferably KOH in a hydroxylated solvent like methanol. The catalyst is filtered off, and the filtrate is evaporated to give the o-phenylene derivative, which is used in the next step without additional purification.

Step (f) involves reacting the o-phenylene diamine derivative as shown in Formula (6) with an oxalic acid derivative like dimethyl oxalate in a hydroxylated or ethereal solvent, preferably THF at reflux temperature. Reaction carried out for about 12 to 24 hours, preferably 16 hours and partially evaporated to give a crude product which is purified by crystallization.

Step (g) involves hydrogenation ($H_2$, 50 psi) of the benzylamine quinoxaline 2,3-dione intermediate as shown in Formula (7) using Pd/C (5–20%), preferably Pd/C (20%) as a catalyst in a polar solvent like DMF or methanol. The suspension was filtered, and the filtrate was evaporated to give a solid, which was crystallized from a hydroxylated solvent like methanol.

Step (h) involves nitration of the quinoxaline 2,3-dione derivative shown in Formula (8) using potassium nitrate or nitric acid, preferably potassium nitrate as the nitrating agent. The reaction is carried out in an acidic solvent like sulfuric acid from temperatures ranging from 0° C. to room temperature. Reaction mixture is poured in ice, and the precipitate obtained is filtered and air dried.

Step (i) involves acylation of the N-methyl benzylamine moiety of quinoxaline 2,3-dione shown in Formula (9). The reaction is carried out with an acylating agent, which is typically an acid chloride or an anhydride, preferably an acid chloride in the presence of a tertiary amine base like triethylamine in a polar solvent like dimethylformamide. Reaction carried from 2 to 18 hours depending on the electrophile, preferably around 16 hours. Reaction mixture is evaporated to dryness, and the residue is treated with aqueous $NaHCO_3$ and filtered. The desired amide was purified by crystallization or chromatography ($SiO_2$) using $CHCl_3$:MeOH mixture as the eluent.

These general experimental schemes cover most of the final products of the invention. Others are made by known experimental procedures.

The above methodology can be used to synthesize amides of the invention as follows:

SCHEME 1

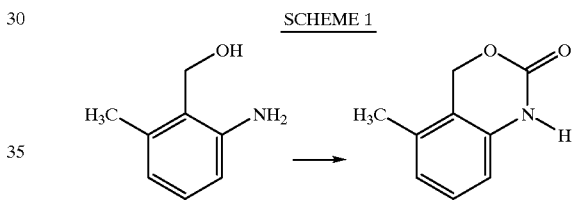

5-Methyl-1,4-dihydro-benzo[d][1,3]-oxazin-2-one

To a solution of (2-amino-6-methyl-phenyl)-methanol (2.74 g, 20 mmol) and triethylamine (4.04 g, 40 mmol) in THF (150 mL), phosgene (12.5% solution in toluene, 17.42 g, 22 nmol) was added dropwise at 0° C. Reaction mixture was allowed to warm to room temperature and stirred for 16 hours. Water (150 mL) was added under stirring, followed by EtOAc (2×100 mL). EtOAc extracts were washed with water and brine and dried over $MgSO_4$. The product (buff solid) was crystallized from EtOAc:pet. ether mixture.

(Yield: 2.37=73%); mp 222–226° C.; MS (CI): M+1=163.

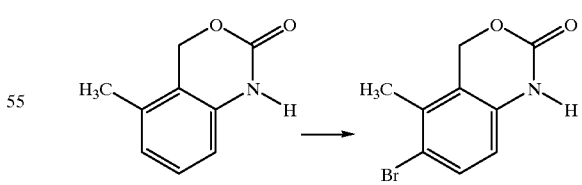

6-Bromo-5-methyl-1,4-dihydro-benzo[d][1,3]oxazine-2-one

To a solution of 5-methyl-1,4-dihydro-benzo[d] [1,3] oxazin-2-one (0.695 g, 4.3 mmol) in acetic acid (5 mL), $Br_2$ (0.805 g=5 mmol) solution in TFA (5 mL)+acetic acid (5 mL) was added at 10° C. Reaction mixture was stirred for 2 hours and poured over ice water. Yellow precipitate was filtered and dried at 120° C.

(Yield: 0.941 g=90%); MS (CI): M+1=243; M+2=244.

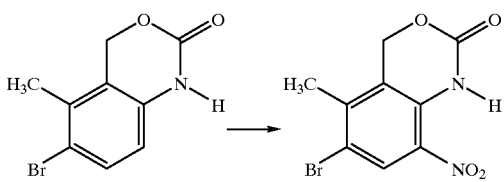

6-Bromo-5-methyl-8-nitro-1,4-dihydro-benzo[d][1,3]-oxazin-2-one

To a solution of 6-bromo-5-methyl-1,4-dihydro-benzo[d][1,3]oxazin-2-one (0.726 g, 3 mmol) in concentrate $H_2SO_4$ (4 mL), $KNO_3$ (0.303 g, 3 mmol) was added at 0° C. Reaction mixture stirred 14 hours and poured over crushed ice. Yellow precipitate was obtained, which was filtered and dried.

(Yield: 0.782=91%); MS (CI): M+1=288; M+2=289.

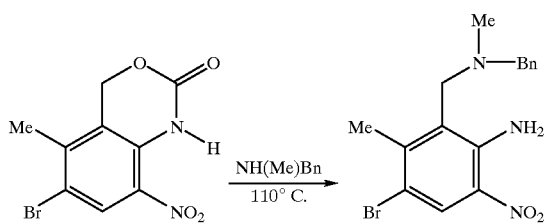

2-[(Benzyl-methyl-amino)-methyl]-4-bromo-3-methyl-6-nitro-phenylamine

6-Bromo-5-methyl-8-nitro-1,4-dihydro-benzo[d][1,3]oxazine-2-one (11.48 g, 40 mmol) was heated to 140° C. for 18 hours. TLC ($SiO_2$, pet. ether:EtOAc, 1:1) indicated completion. Volatile material concentrated on rotavap and the dark oil extracted with ethyl acetate (2×250 mL). Solvent evaporated to give viscous oil, which on trituration with ethyl acetate (150 mL) gave yellow crystalline product.

Yield in two crops: 10.17 g=70%; MS (CI): M+1=364; Elemental analysis calculated for $C_{16}H_{18}BrN_3O_2$:
C, 52.76; H, 4.98; N, 11.54.
Found: C, 52.22; H, 4.87; N, 11.11.

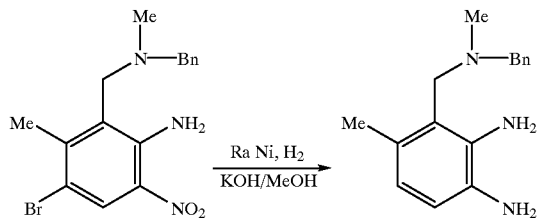

3-[(Benzyl-methyl-amino)-methyl]-4-methyl-benzene-1,2-diamine

2-[(Benzyl-methyl-amino)-methyl]-4-bromo-3-methyl-6-nitro-phenylamine (6 g, 16.5 mmol) was hydrogenated (Ra Ni, 3 g) in the presence of KOH (0.498N). Reaction mixture filtered and extracted in $CHCl_3$ (200 mL) and washed with water and dried ($MgSO_4$). Solvent evaporated to give a dark oil 4.19 g=99%.

H-NMR: 1.96 (s, 3H), 2.08 (s, 3H), 3.36–3.39 (m, 4H), 4.23 (s, 2H), 4.73 (s, 2H), 6.18 (d, 1H, J=7.3 Hz), 6.33 (d, 1H, J=7.3 Hz), 7.21–7.26 (m, 5H).

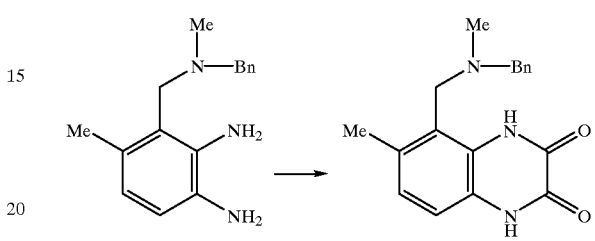

5-[(Benzyl-methyl-amino)-methyl]-6-methyl-1,4-dihydrqouinoxaline-2,3-dione

To a solution of diamine (4.19 g) in THF, dimethyl oxalate (2.36 g, 20 mmol) was added. Reaction mixture stirred at reflux for 16 hours and cooled. Buff ppt was filtered (2.93 g). Mother liquor gave two additional crops. Total yield: 3.945 g=77.4%; mp 205–206° C.; MS (CI): M+1=310.

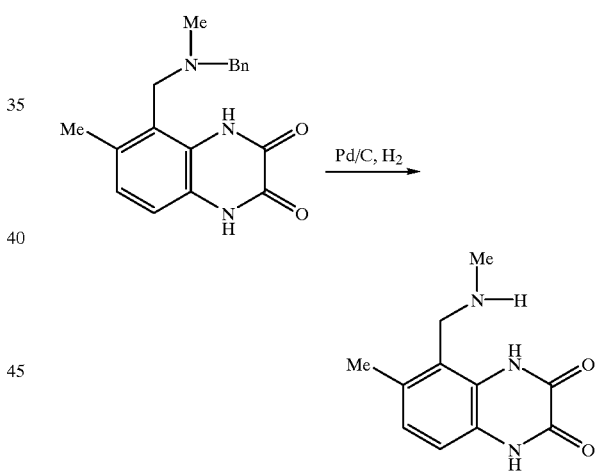

6-Methyl-5-methylaminomethyl-1,4-dihydro-quinoxaline-2,3-dione

A solution of 5-[(benzyl-methyl-amino)-methyl]-6-methyl-1,4-dihydro-quinoxaline-2,3-dione (3.23 g, 10.45 mmol) in DMF (100 mL) was hydrogenated (Pd/C, 20%, 0.5 g) in DMF (100 mL). The suspension was filtered, and the filtrate was evaporated to give a solid, which was crystallized from methanol.

Yield: 1.276 g=56%. MS (CI): M+1=220.

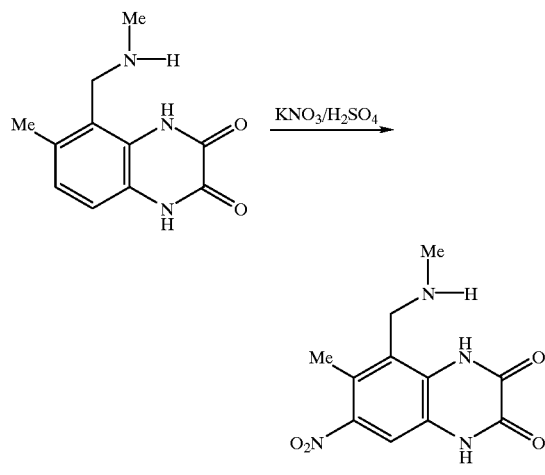

6-Methyl-5-methylaminomethyl-7-nitro-1,4-dihydro-quinoxaline-2,3-dione H$_2$SO$_4$ salt To a cooled (10° C.) solution of 6-methyl-5-methylaminomethyl-1,4-dihydro-quinoxaline-2,3-dione (10° C.) of (1.23 g, 5.6 mmol) in concentrate H$_2$SO$_4$ (5 mL), KNO$_3$ (0.606 g, 6 mmol) was added. Reaction mixture stirred overnight and quenched with ice. Green ppt filtered and washed with ice-cold water and dried to give sulfate salt (0.77 g, 42%); mp 260–261° C. MS (CI): M+1=265.

General Method for the Synthesis of N-methyl Amides

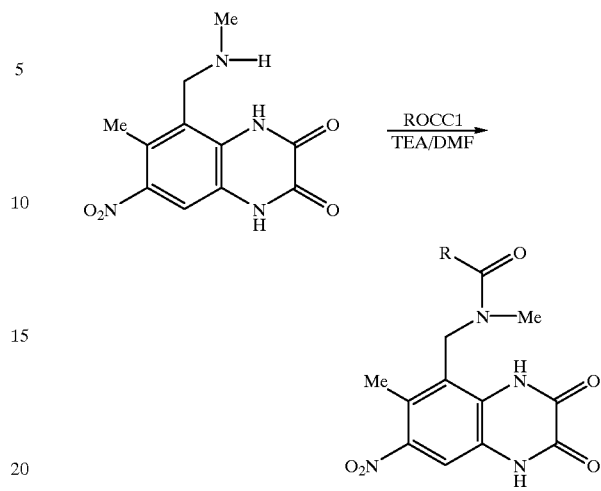

To a solution of 6-methyl-5-methylaminomethyl-7-nitro-1,4-dihydro-quinoxaline-2,3-dione (0.1 mmol) and triethylamine (0.25 mnuol) in DMF (2 mL), appropriate acid chloride (0.22 mmol) was added. Reaction mixture was stirred for 16 hours and evaporated. The residue was treated with water and filtered. The product was further washed with water (3×5 mL) and dried. The final product was purified by column chromatography (SiO$_2$, CHCl$_3$:MeOH, 100% to 95:5).

TABLE 4

N-Methyl Amide Derivatives of Quinoxaline 2,3-dione

| Compound | Structure | Yield % | MS (CI, M + 1) |
|---|---|---|---|
| N-Methyl-N-(6-methyl-7-nitro-2,3-dioxo-1,2,3,4-tetrahydro-quinoxalin-5-ylmethyl)-acetamide | 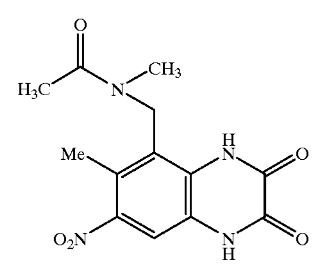 | 41 | 307 |
| 5-(Isopropyl-methyl-amino)-methyl-6-methyl-7-nitro-1,4-dihydro-quinoxaline-2,3-dione | 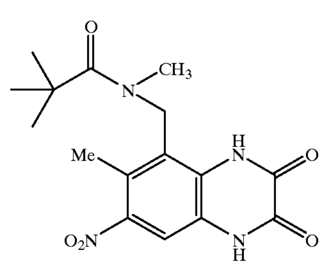 | 16 | 349 |

TABLE 4-continued

N-Methyl Amide Derivatives of Quinoxaline 2,3-dione

| Compound | Structure | Yield % | MS (CI, M + 1) |
|---|---|---|---|
| Cyclohexanecarboxylic acid-methyl-(6-methyl-7-nitro-2,3-dioxo-1,2,3,4-tetrahydro-quinoxalin-5-ylmethyl)amide | 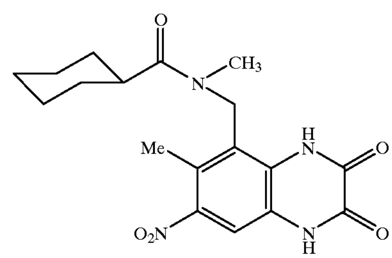 | 35 | 375 |
| 2-Cyclohexyl-N-methyl-N-(6-methyl-7-nitro-2,3-dioxo-1,2,3,4-tetrahydro-quinoxalin-5-ylmethyl)-acetamide | 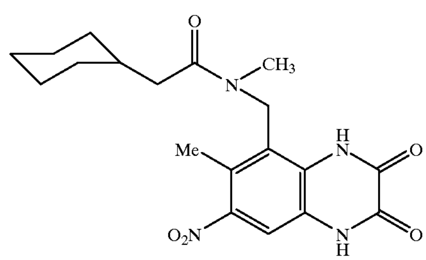 | 91 | 361 |
| N-methyl-N-(6-methyl-7-nitro-2,3-dioxo-1,2,3,4-tetrahydro-quinoxalin-5-ylmethyl)-2-phenyl-acetamide | 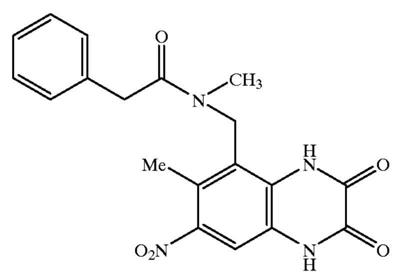 | 24 | 383 |
| N-methyl-N-(6-methyl-7-nitro-2,3-dioxo-1,2,3,4-tetrahydro-quinoxalin-5-ylmethyl)-benzamide | 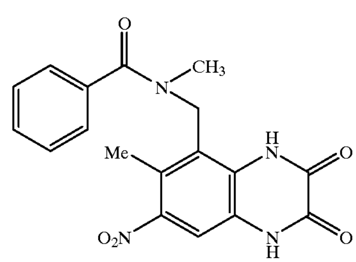 | 71 | 369 |
| 4-Chloro-N-methyl-N-(6-Methyl-7-nitro-2,3-dioxo-1,2,3,4-tetrahydro-quinoxalin-5-ylmethyl)-benzamide | 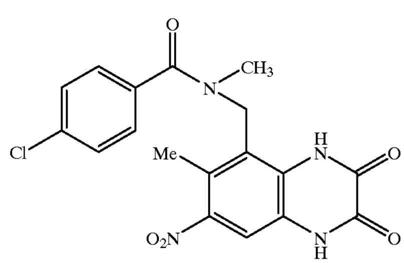 | 65 | 403 |

TABLE 4-continued

N-Methyl Amide Derivatives of Quinoxaline 2,3-dione

| Compound | Structure | Yield % | MS (CI, M + 1) |
| --- | --- | --- | --- |
| N-Methyl-N-(6-Methyl-7-nitro-2,3-dioxo-1,2,3,4-tetrahydro-quinoxalin-5-ylmethyl)-4-trifluoromethyl-benzamide | 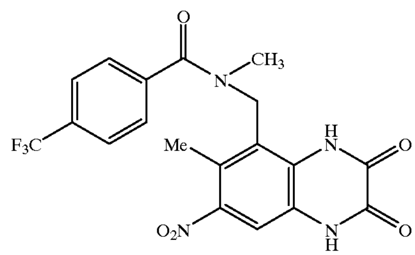 | 38 | 437 |
| 3,4-Dichloro-N-methyl-N-(6-methyl-7-nitro-2,3-dioxo-1,2,3,4-tetrahydro-quinoxalin-5-ylmethyl)-benzamide | 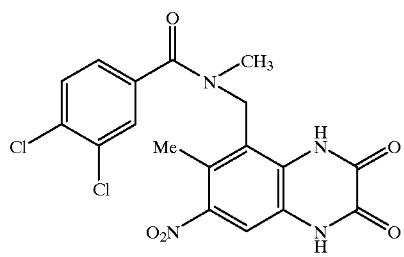 | 56 | 437 |
| N-Methyl-N-(6-Methyl-7-nitro-2,3-dioxo-1,2,3,4-tetrahydro-quinoxalin-5-ylmethyl)-4-nitro-benzamide | 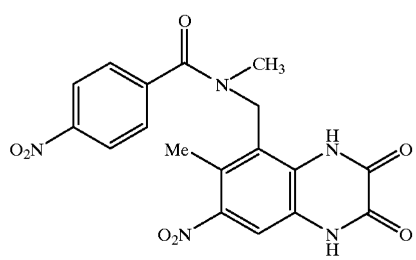 | 87 | 414 |
| Thiophene-2-carboxylic acid-methyl-(6-methyl-7-nitro-2,3-dioxo-1,2,3,4-tetrahydro-quinoxalin-5-ylmethyl)-amide | 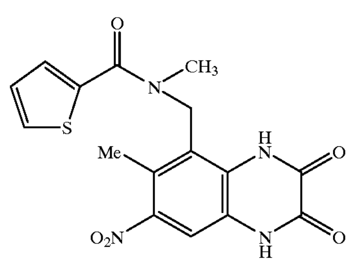 | 90 | 375 |
| Furan-2-carboxylic acid methyl-(6-methyl-7-nitro-2,3-dioxo-1,2,3,4-tetrahydro-quinoxalin-5-ylmethyl)-amide | 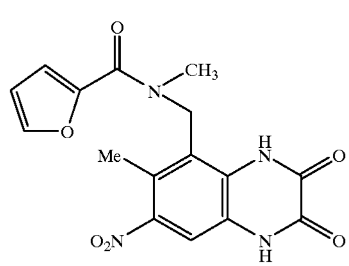 | 22 | 359 |

TABLE 4-continued

N-Methyl Amide Derivatives of Quinoxaline 2,3-dione

| Compound | Structure | Yield % | MS (CI, M + 1) |
|---|---|---|---|
| Benzo[b]thiophene-2-carboxylic acid methyl-(6-methyl-7-nitro-2,3-dioxo-1,2,3,4-tetrahydro-quinoxalin-5-ylmethyl)-amide | 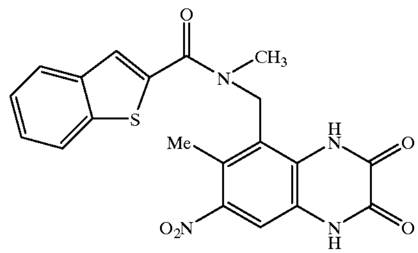 | 38 | 437 |
| 4-Methoxy-N-methyl-N-(6-methyl-7-nitro-2,3-dioxo-1,2,3,4-tetrahydro-quinoxalin-5-ylmethyl)-benzamide | 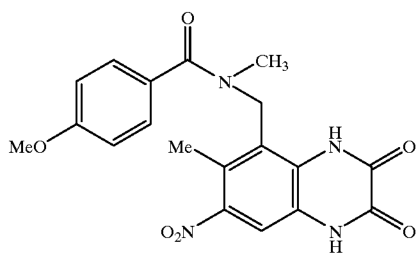 | 67 | 399 |
| Methyl-(6-methyl-7-nitro-2,3-dioxo-1,2,3,4-tetrahydro-quinoxalin-5-ylmethyl)-carbamic acid ethyl ester | 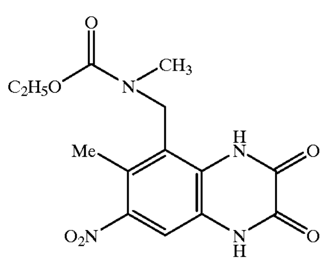 | 64 | 337 |

We claim:

1. A compound of Formula I

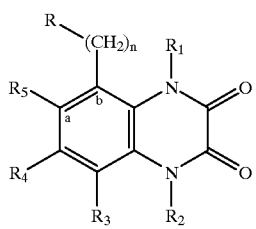

wherein

R is

attached at N to the quinoxaline ring through —(CH$_2$)$_n$— at the b-position,

X is methyl;

Y is alkyl, cycloalkyl, cycloalkylalkyl, heteroaryl, selected from the group consisting of 2- or 3-benzfuryl, 2- or 3-indolyl, 2- or 3-furanyl, 2- or 3- thienyl 2-, 3-, 4-, 5-, 6-, or 7-benzothienyl, aralkyl, aryl, heterocycloalkyl selected from the group consisting of 2- or 3-pyrrolidinyl, 2- or 3-tetrahydrofuranyl, and 2-, 3-, or 4-piperidinyl;

or is —(CH)$_p$(R$_{24}$)C(O)NR$_{25}$R$_{26}$ wherein p is an integer of from 1 to 6, R$_{24}$ is hydrogen and R$_{25}$ and R$_{26}$ are each independently hydrogen, alkyl;

or is —(CH$_2$)$_q$—R$_{27}$ wherein q is an integer from 1 to 3 and R$_{27}$ is a 4- to 7-membered heterocycle containing from one to four heteroatoms selected from oxygen, sulfur, and nitrogen, wherein said heterocycle is heterocycloalkyl selected from 2- or 3-pyrrolidinyl, 2- or 3-tetrahydrofuranyl, and 2-, 3-, or 4-piperidinyl, or heteroaryl selected from oxazolyl, oxadiazolyl, thiazolyl, 1,3,4-oxadiazolyl, 1,2,4-triazolyl, 1,3,4-thiadiazolyl, pyrrazolyl, imidazolyl, tetrazolyl, 1,3-oxazolyl, isoxazolyl, 1,2,3-triazolyl, 1,3,4-thiazolyl, or is —NR$_{27a}$—R$_{27b}$ wherein 27a is hydrogen or alkyl, and 27b is as described in R$_{27}$;

n is 1;

R$_1$ is hydrogen;

R$_2$ is hydrogen;

R$_3$ is hydrogen:

R$_4$ is nitro, and

R$_5$ is methyl and is at the a-position.

2. A compound according to claim 1 wherein R is

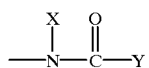

wherein

X is selected from methyl and

Y is selected from alkyl, cycloalkyl, heterocycloalkyl selected from the group consisting of 2- or 3-pyrrolidinyl, 2- or 3-tetrahydrofuranyl, and 2-, 3-, or 4-piperidinyl, aryl, heteroaryl selected from the group consisting of 2- or 3-furanyl, 2- or 3-thienyl 2-, 3-, 4-, 5-, 6-, or 7-benzothienyl, cycloalkylalkyl, aralkyl;

or is —(CH)$_p$(R$_{24}$)C(O)NR$_{25}$R$_{26}$ wherein p is an integer of from 1 to 6, R$_{24}$ is hydrogen and R$_{25}$ and R$_{26}$ are each independently hydrogen, alkyl;

or is —(CH$_2$)$_q$—R$_{27}$ wherein q is an integer from 1 to 3 and R$_{27}$ is a 4- to 7-membered oxygen, nitrogen, sulfur heterocycle with 1- to 4 heteroatoms selected from oxadiazolyl, thiazolyl, oxazolyl, and tetrazolyl.

3. A compound according to claim 2 wherein R is

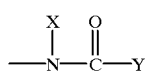

wherein

X is selected from methyl and

Y is selected from methyl, ethyl, isopropyl, propyl, butyl, benzyl, cyclopentyl, cyclohexyl, cyclohexylmethyl, 2-(N,N-dimethylaminocarbonyl)-ethyl, 2- or 3-pyrrolidinyl, 2- or 3-tetrahydrofuranyl, 2-, 3-, or 4-piperidinyl, substituted phenyl, 2- or 3-furanyl, 2- or 3-thienyl, 2- or 3-benzfuranyl, 2- or 3-benzthienyl, 2- or 3-indolyl, imidazolyl, phenyl, tetrazolyl, pyrrazolyl, naphthyl, oxadiazolyl, and 2-benzimidazolyl.

4. A compound according to claim 1 selected from the group consisting of

N-Methyl-N-(6-methyl-7-nitro-2,3-dioxo-1,2,3,4-tetrahydro-quinoxalin-5-ylmethyl)-acetamide, Cyclohexanecarboxylic acid-methyl-(6-methyl-7-nitro-2,3-dioxo-1,2,3,4-tetrahydro-quinoxalin-5-ylmethyl) amide, N-methyl-N-(6-methyl-7-nitro-2,3-dioxo-1,2,3,4-tetrahydro-quinoxalin-5-ylmethyl)-2-phenyl-acetamide, N-methyl-N-(6-methyl-7-nitro-2,3-dioxo-1,2,3,4-tetrahydro-quinoxalin-5-ylmethyl)-benzamide, 4-Chloro-N-methyl-N-(6-Methyl-7-nitro-2,3-dioxo-1,2,3,4-tetrahydro-quinoxalin-5-ylmethyl)-benzamide, N-Methyl-N-(6-Methyl-7-nitro-2,3-dioxo-1,2,3,4-tetrahydro-quinoxalin-5-ylmethyl)-4-trifluoromethyl-benzamide, 3,4-Dichloro-N-methyl-N-(6-methyl-7-nitro-2,3-dioxo-1,2,3,4-tetrahydro-quinoxalin-5-ylmethyl)-benzamide, N-Methyl-N-(6-Methyl-7-nitro-2,3-dioxo-1,2,3,4-tetrahydro-quinoxalin-5-ylmethyl)-4-nitro-benzamide, Thiophene-2-carboxylic acid-methyl-(6-methyl-7-nitro-2,3-dioxo-1,2,3,4-tetrahydro-quinoxalin-5-ylmethyl)-amide, Furan-2-carboxylic acid-methyl-(6-methyl-7-nitro-2,3-dioxo-1,2,3,4-tetrahydro-quinoxalin-5-ylmethyl)-amide, Benzo[b]thiophene-2-carboxylic acid methyl-(6-methyl-7-nitro-2,3-dioxo-1,2,3,4-tetrahydro-quinoxalin-5-ylmethyl)-amide, 4-Methoxy-N-methyl-N-(6-methyl-7-nitro-2,3-dioxo-1,2,3,4-tetrahydro-quinoxalin-5-ylmethyl)-benzamide, N,N,N'-Trimethyl-N'-(6-methyl-7-nitro-2,3-dioxo-1,2,3,4-tetrahydro-quinoxalin-5-ylmethyl)-succinamide, and Methyl-(6-methyl-7-nitro-2,3-dioxo-1,2,3,4-tetrahydro-quinoxalin-5-ylmethyl)-carbamic acid ethyl ester.

5. A compound named 2-Cyclohexyl-N-methyl-N-(6-methyl-7-nitro-2,3-dioxo-1,2,3,4-tetrahydro-quinoxalin-5-ylmethyl)-acetamide.

6. A compound named Methyl-(6-methyl-7-nitro-2,3-dioxo-1,2,3,4-tetrahydro-quinoxalin-5-ylmethyl)-carbamic acid ethyl ester.

7. A pharmaceutical composition comprising a therapeutically effective amount of a compound according to claim 1 together with a pharmaceutically acceptable carrier in unit dosage form.

8. A method for treating convulsions which comprises administering a therapeutically effective amount of a compound according to claim 1 to a patient in need of said treatment.

9. A process for the preparation of a compound of Formula I according to claim 1 comprising:

(a) reacting an aminobenzyl alcohol of formula

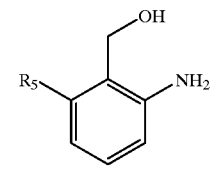

1 wherein R$_5$ is methyl with an acylating agent at temperatures from −10° C. to room temperature and stirring for from 2 to 16 hours to produce a cyclic carbamate of formula

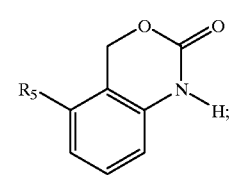

2

(b) brominating the product of Step (a) above to give a compound of formula

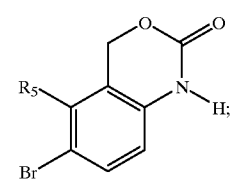

3

(c) nitrating the product of Step (b) above to give a compound of formula

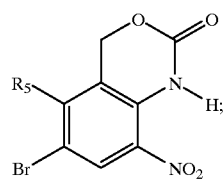

4

(d) reacting the product of Step (c) above with a secondary amine of formula

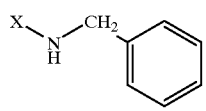

wherein X is as defined in claim 2 at elevated temperatures for about 18 hours to produce the desired benzylamine derivative of formula

5

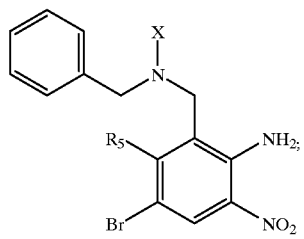

(e) hydrogenating the product of Step (d) above in the presence of a catalyst and a base to produce the desired diamine of formula

6

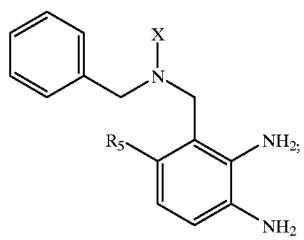

(f) reacting the diamine from Step (e) above with an oxalic acid derivative at reflux temperatures for 12 to 24 hours to produce the quinoxaline-2,3-dione intermediate of formula

7

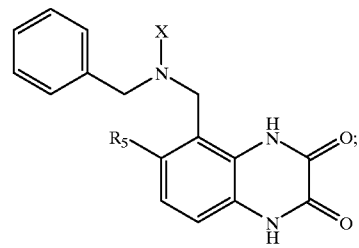

(g) hydrogenating the intermediate from Step (f) above using a catalyst in a polar solvent to produce a desired secondary amine derivative of formula

8

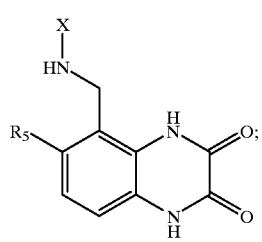

(h) nitrating the compound of Step (g) above in an acidic solvent to produce the nitro derivative of formula

9

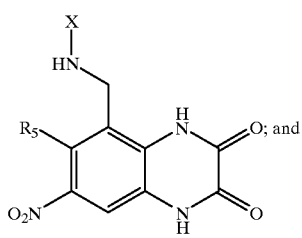

(i) acylating the product of Step (h) above in the presence of a tertiary amine base to produce the desired compound of the invention of formula

I

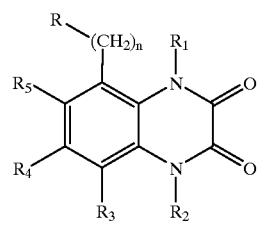

wherein n, R, and $R_1$—$R_5$ are as defined in claim 1.

* * * * *